US009925364B2

(12) United States Patent
Khalaj et al.

(10) Patent No.: US 9,925,364 B2
(45) Date of Patent: Mar. 27, 2018

(54) CATHETER CONNECTOR INSERT (71) Applicant: Avent, Inc., Alpharetta, GA (US)

(72) Inventors: Steve Saeed Khalaj, Laguna Hills, CA (US); Kenneth Chen-Tse Hsu, Tustin, CA (US)

(73) Assignee: Avent, Inc., Alpharetta, GA (US)

( * ) Notice: Subject to any disclaimer, the term of this patent is extended or adjusted under 35 U.S.C. 154(b) by 338 days.

(21) Appl. No.: 14/282,087

(22) Filed: May 20, 2014

(65) Prior Publication Data

US 2015/0335873 A1 Nov. 26, 2015

(51) Int. Cl.
*A61M 39/10* (2006.01)
*A61M 25/00* (2006.01)
(Continued)

(52) U.S. Cl.
CPC ............ *A61M 39/10* (2013.01); *A61M 25/00* (2013.01); *A61M 39/12* (2013.01);
(Continued)

(58) Field of Classification Search
CPC ...... A61M 39/10; A61M 25/00; A61M 39/12; A61M 2039/087; A61M 2039/1033; A61M 2039/1038
See application file for complete search history.

(56) References Cited

U.S. PATENT DOCUMENTS

| 4,323,065 | A | 4/1982 | Kling |
| 5,792,105 | A | 8/1998 | Lin et al. |

(Continued)

FOREIGN PATENT DOCUMENTS

EP 0 190 388 A2 8/1986

OTHER PUBLICATIONS

PCT Search Report, Aug. 3, 2015.

*Primary Examiner* — Emily Schmidt
*Assistant Examiner* — Lauren M Peng
(74) *Attorney, Agent, or Firm* — Dority & Manning, P.A.

(57) ABSTRACT

The present invention relates to a catheter connector configured to provide an escape location for a liquid medium trapped therein. The catheter connector includes a body having a proximal end and a distal end. The proximal end includes a proximal end port for mating communication with a fluid delivery device. The body defines a hollow interior extending from the proximal end to the distal end. In one embodiment, the catheter connector includes an insert configured within the hollow interior of the connector. The insert defines a bore therethrough that is configured to receive a catheter at least partially therein. Further, the bore includes an interior wall and an exterior wall defining a thickness therebetween. The interior wall includes at least one discontinuity. Thus, when the catheter is inserted through the bore, at least one cavity is formed by the catheter and the at least one discontinuity of the insert. The cavity is configured to collect a liquid medium within the catheter connector, thereby maintaining a secure connection between the catheter and the catheter connector. In another embodiment, the hollow interior of the catheter connector may be manufactured with at least one discontinuity so as to form a cavity configured to collect a liquid medium within the catheter connector.

19 Claims, 5 Drawing Sheets (A)

(B)

(51) Int. Cl.
*A61M 39/12* (2006.01)
*A61M 39/08* (2006.01)

(52) U.S. Cl.
CPC .............. *A61M 2039/087* (2013.01); *A61M 2039/1033* (2013.01); *A61M 2039/1038* (2013.01)

(56) References Cited

U.S. PATENT DOCUMENTS

| | | |
|---|---|---|
| 5,989,240 A | 11/1999 | Strowe |
| 7,883,502 B2 | 2/2011 | Powers et al. |
| 8,611,993 B2 | 12/2013 | Vitullo et al. |
| 8,617,138 B2 | 12/2013 | Barron et al. |
| 2002/0032436 A1 | 3/2002 | Mogg |
| 2012/0253322 A1* | 10/2012 | Barron .............. A61M 25/0014 604/535 |
| 2015/0119855 A1 | 4/2015 | Khalaj |

\* cited by examiner

CATHETER CONNECTOR INSERT

FIELD OF THE INVENTION

The present invention relates generally to the field of medical catheters and more particularly to catheter connector inserts.

BACKGROUND

The use of catheters to deliver or withdraw fluids from a patient for various medical procedures is well known. For example, U.S. Pat. No. 7,959,623 describes a pain management system that uses various embodiments of infusion catheters to deliver fluid medication from a pump, through tubing, to a wound site. With such configurations, catheter connectors are typically used to connect the catheter to various devices, such as tubing, a fluid reservoir or other fluid delivery device, and so forth. In the system of the '623 patent, a conventional Tuohy-Borst connector is used to connect the distal end of a medical tube to the proximal end of the catheter.

In addition to Tuohy-Borst connectors, various other configurations of catheter connectors are available. For example, Epimed International of Farmers Branch, Tex., USA, manufactures a low profile twist-lock catheter connector known as the "Stingray™ Connector." This device has axially aligned halves that twist to an open position to allow insertion of the catheter in a first half, and subsequently twist to a closed position with an audible and tactile click that indicates complete engagement with the catheter. The second half connects to a tube or other fluid delivery device for delivering fluid through the connector to the catheter.

Smiths Medical International Ltd. of the United Kingdom offers a catheter connector under the "EpiFuse™" trade name that consists of two halves joined by a living hinge. A catheter is inserted into a hole at the base of the connector and is retained when the two halves are folded and locked together.

Coupling of the catheter connector to the catheter needs to be quick and easy, as there is little to no time for a doctor or nurse to adjust and/or study the device. In addition, it is important that the connection between the catheter connector and the catheter remains stable and uncompromised during various medical procedures. For example, during some medical procedures, the catheter may be coated with an ultrasonic gel before being inserted into the patient. As such, the proximal end of the atheter (i.e. the end of the catheter that is inserted into the catheter connector) may become contaminated with gel. Thus, when the catheter connector is attached to the catheter, oftentimes, the catheter will not connect properly. In addition, other liquid mediums, such as medicines, blood, saliva, or similar, may become trapped inside the catheter connector, thereby compromising the connection between the catheter connector and the catheter.

As such, the medical art is continuously seeking new and improved catheter connectors that provide quick and reliable connection. Accordingly, the present invention provides a catheter connector that addresses the aforementioned problems.

SUMMARY OF THE INVENTION

Objects and advantages of the invention will be set forth in part in the following description, or may be obvious from the description, or may be learned through practice of the invention.

In certain aspects, the present invention relates to a catheter connector. The catheter connector includes a body having a proximal end and a distal end. The proximal end includes a proximal end port for mating communication with a fluid delivery device, such as a pump, reservoir, syringe, or the like. This port may have any conventional configuration, such as a Luer-lock fitting. The body defines a hollow interior extending from the proximal end to the distal end. An insert is configured within the hollow interior and defines a bore therethrough. The bore is configured to receive a catheter at least partially therethrough. The bore includes an interior wall and an exterior wall defining a thickness therebetween. In addition, the interior wall includes at least one discontinuity. Thus, when the catheter is inserted through the bore, at least one cavity is formed by the catheter and the at least one discontinuity of the insert. The cavity is configured to collect and/or receive a liquid medium within the catheter connector, thereby maintaining a secure connection between the catheter and the catheter connector.

In a further embodiment, the exterior wall of the insert may be configured within the hollow interior of the body of the catheter connector so as to provide a friction fit between the insert and the connector. In additional embodiments, the interior wall of the bore of the insert may include a plurality of discontinuities spaced circumferentially about the interior wall. Thus, the one or more discontinuities may extend from the bore of the insert through the entire thickness of the insert and through the exterior wall. Alternatively, the one or more discontinuities may extend from the bore through only a portion of the thickness of the insert. In certain embodiments, the discontinuities may be spaced equally about the interior wall. In alternative embodiments, the plurality of discontinuities may be spaced randomly about the interior wall.

In still additional embodiments, the discontinuities may include at least one of or a combination of the following: a rib, a ridge, a protrusion, a peak, a valley, a cavity, a channel, a through hole, an aperture, a void, or similar. For example, in one embodiment, the discontinuities may include a plurality of peaks spaced apart circumferentially about the interior wall by a plurality of valleys. More specifically, in one embodiment, each of the plurality of peaks and each of the plurality of valleys may include at least one non-arcuate edge. Alternatively, each of the plurality of peaks and each of the plurality of valleys include at least one arcuate edge. In such an embodiment, when the catheter is inserted through the bore, a plurality of cavities are formed by the catheter and the plurality of peaks.

In further embodiments, the cavities may have any suitable size and/or shape so as to receive and/or collect a liquid medium from within the catheter connector. For example, in certain embodiments, each of the plurality of cavities include a triangular cross-section. In further embodiments, the cavities may have a square or rectangular cross-section. In still further embodiments, the cavities may have a rounded or circular cross-section.

In additional embodiments, the insert may be constructed of a flexible material. For example, in certain embodiments, the flexible material may include at least one of or a combination of the following: a rubber material, a polymeric material, a silicone material, an elastomeric material, or similar. In another aspect, the present invention relates to a catheter connector configured to provide an escape location for a liquid medium trapped therein. More specifically, the catheter connector includes a body having a proximal end and a distal end. The body defines a hollow interior extending from the proximal end to the distal end. The connector also includes a proximal end port configured with the proximal end of body for mating communication with a fluid delivery device. The hollow interior of the connector defines a bore therethrough. The bore is configured to receive a catheter at least partially therethrough and includes an interior wall having at least one discontinuity. Thus, when the catheter is inserted through the bore of the connector, at least one cavity is formed by the catheter and the at least one discontinuity. Accordingly, the cavity is configured to collect a liquid medium therein. It should be understood that the connector may further include any one of or combinations of the features described herein.

In further aspects, the present invention relates to an insert for a catheter connector. The insert includes a body configured to fit within a hollow interior of the catheter connector. The body has a proximal end and a distal end. Further, the body includes a bore extending therethrough from the proximal end to the distal end. The bore is configured to receive a catheter at least partially therethrough. In addition, the bore includes an interior wall having at least one discontinuity. It should be understood that the insert may further include any one of or combinations of the features described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The positional terms "proximal" and "distal" are used herein to orient the various components relative to each other and to the patient. "Distal" refers to the direction that is closest to the wound site (e.g., the distal end of the connector is the end oriented towards a catheter insertion site), and "proximal" refers to the opposite direction (e.g., the proximal end of the catheter is inserted into the distal end of the connector).

Generally, the present disclosure is directed to a catheter connector that is configured to provide an escape location for a liquid medium trapped therein so as to maintain a secure connection between the catheter and the catheter connector. More specifically, in one embodiment, the catheter connector includes an insert having a body configured to fit within a catheter connector. The body has a proximal end and a distal end and a bore extending therethrough. The bore is configured to receive a catheter at least partially therein and includes an interior wall having at least one discontinuity. Thus, when the catheter is inserted through the bore, at least one cavity is formed by the catheter and the discontinuity. The cavity is configured to collect a liquid medium that may be present in the catheter connector, thereby maintaining a secure connection between the catheter and the catheter connector. In an alternative embodiment, the hollow interior of the catheter connector may be manufactured with at least one discontinuity so as to form a cavity configured to collect a liquid medium within the catheter connector. In such an embodiment, the insert can be eliminated.

The present disclosure has many advantages not present in the prior art. For example, the discontinuities or ridges of the insert and/or the connector provide an escape location for a liquid medium, e.g. ultrasonic gel, which may become trapped within the catheter connector. Thus, the liquid medium can escape into the one or more cavities formed by the discontinuities such that proper connection between the catheter and the catheter connector can be maintained. In addition, in certain embodiments, the insert is universal and can be configured to fit within any type of catheter connector.

Figure 1:
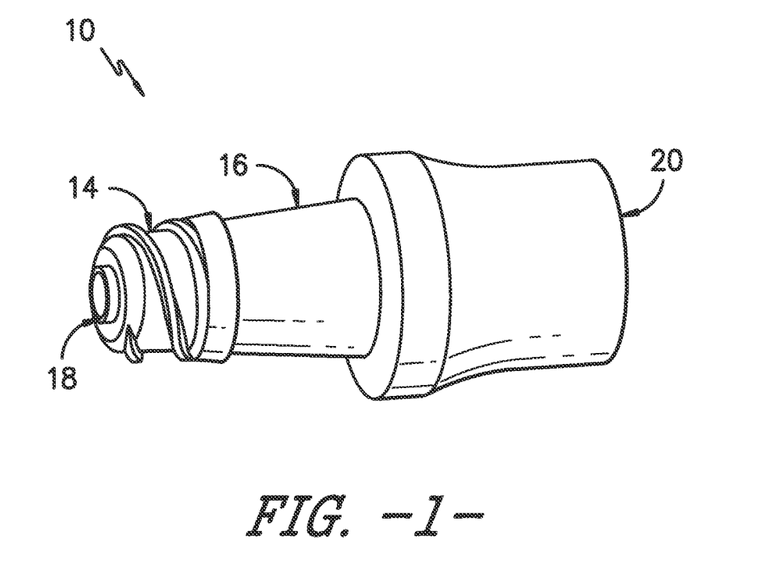
FIG. 1 illustrates a perspective view of one embodiment of a catheter connector in accordance with aspects of the invention.
Figure 2:
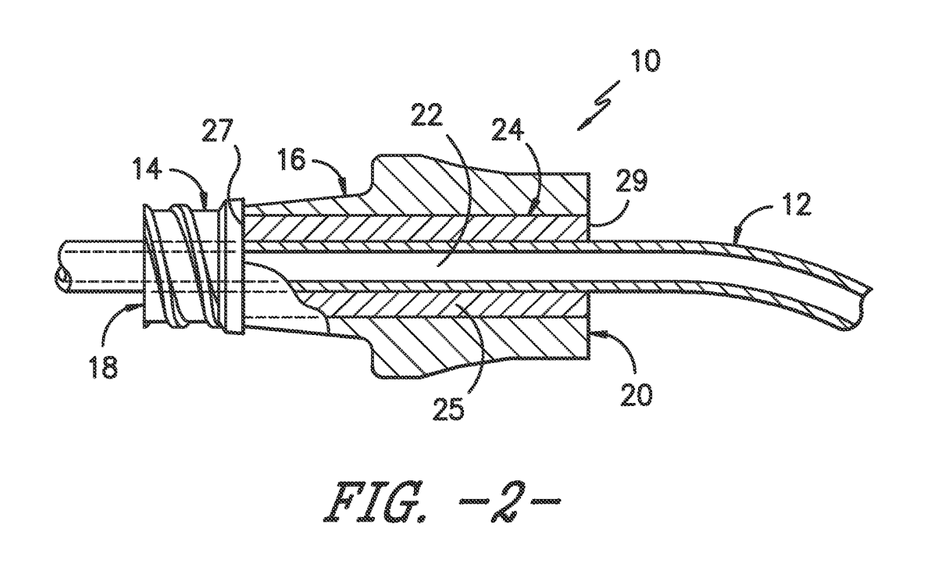
FIG. 2 illustrates a cross-sectional view of one embodiment of a catheter connector in accordance with aspects of the invention.

Referring now to the drawings, FIGS. 1 and 2 illustrate various views of one embodiment of a catheter connector 10 with an insert 24 configured therein according to the present disclosure. As shown, the catheter connector 10 includes a body 16 having a proximal end 18 and distal end 20. The proximal end 18 includes a proximal end port 14 configured thereon for mating communication with a fluid delivery device (not shown). As mentioned, the fluid delivery device may be any suitable device known in the art, such as a pump, reservoir, syringe, or the like. Further, the proximal end port 14 may have any conventional configuration, such as a Luer-lock fitting. In addition, it should be understood that the insert 24 described herein is configured to fit within any suitable connector known in the art and is not limited to the connector 10 of the illustrated embodiment. For example, in various embodiments, the insert 24 may be used with a Tuohy-Borst connector or a Stingray™ connector.

Figure 3:
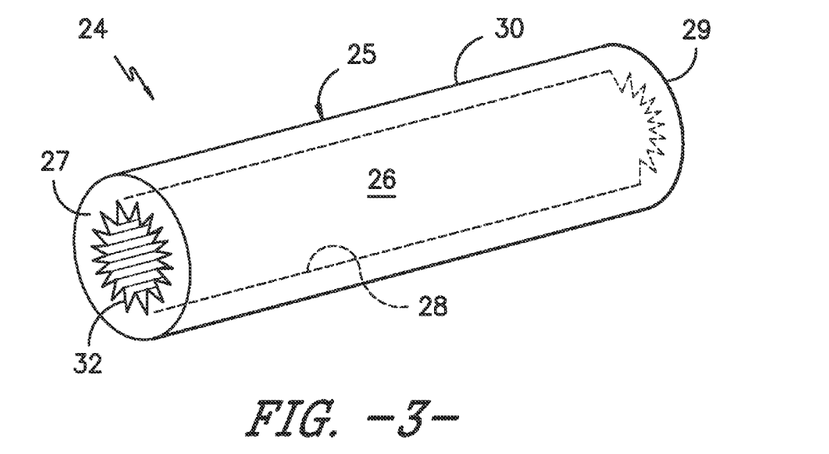
FIG. 3 illustrates a perspective view of one embodiment of a catheter connector insert in accordance with aspects of the invention.
Figure 6:
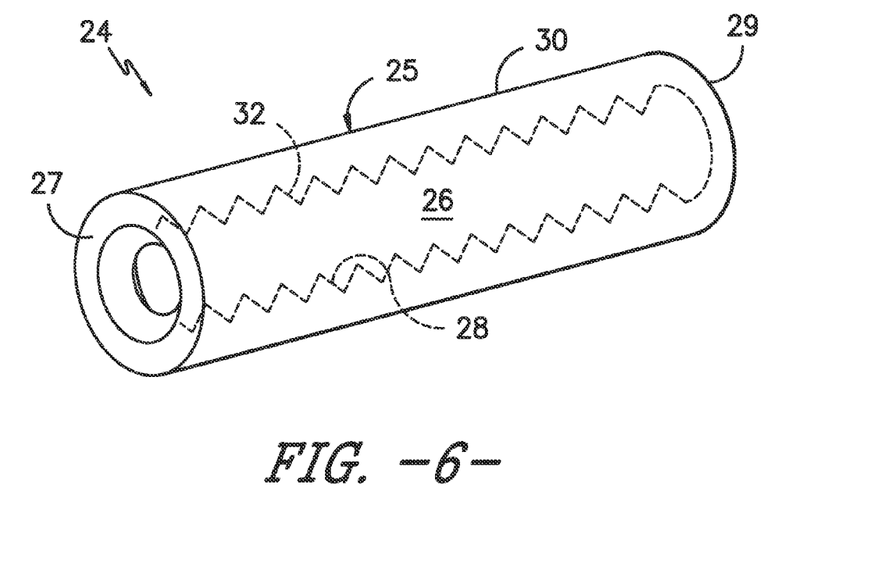
FIG. 6 illustrates a perspective view of another embodiment of a catheter connector insert in accordance with aspects of the invention.

Referring to FIGS. 2, 3, and 6, the insert 24 includes a body 25 having a proximal end 27 and a distal end 29 that correspond to the proximal and distal ends 18, 20 of the connector 10. In addition, the insert 24 includes an interior wall 28 and an exterior wall 30 separated by a thickness 38. Thus, in various embodiments, the dimensions of the exterior wall 30 are designed so as to fit within the hollow interior 22 of the catheter connector 10. More specifically, in certain embodiments, the dimensions of the exterior wall 30 are designed so as to provide a friction fit between the insert 24 and the connector 10. The body 25 of the insert 24 also includes a bore 26 extending therethrough from the proximal end 27 to the distal end 29 that is configured to receive a catheter 12 at least partially therein.

Figure 4:
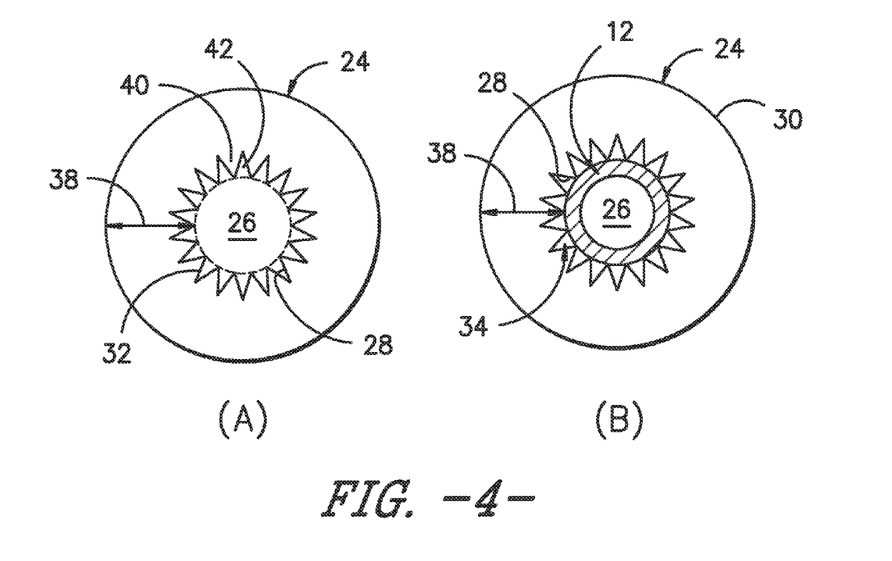
FIG. 4 illustrates various front, cross-sectional views of one embodiment of the catheter connector insert with and without the catheter inserted therethrough in accordance with aspects of the invention.

Referring particularly to FIGS. 3, 4, 6, and 8, the bore 26 defines an interior wall 28 having at least one discontinuity 32. For example, as shown in FIGS. 3 and 4, the interior wall 28 includes a plurality of discontinuities 32 spaced circumferentially about the interior wall 28. Alternatively, as shown in FIG. 6, the interior wall 28 includes a plurality of discontinuities 32 spaced longitudinally along a length of the bore 26 of the insert 24. It should be understood that the discontinuities 32 as described herein may include at least one of or a combination of the following: a rib, a ridge, a protrusion, a peak, a valley, a cavity, a channel, a through hole, an aperture, a void, or similar. For example, as shown in FIG. 4, the discontinuities 32 include a plurality of peaks 40 spaced circumferentially about the interior wall 28. In addition, the peaks 40 may be spaced apart from each other by a plurality of valleys 42. More specifically, as shown in FIGS. 4(A) and 4(B), each of the peaks 40 and each of the valleys 42 include at least one non-arcuate or sharp edge. Alternatively, the peaks 40 and the valleys 42 may include at least one arcuate edge, as shown in FIG. 6(A).

Figure 5:
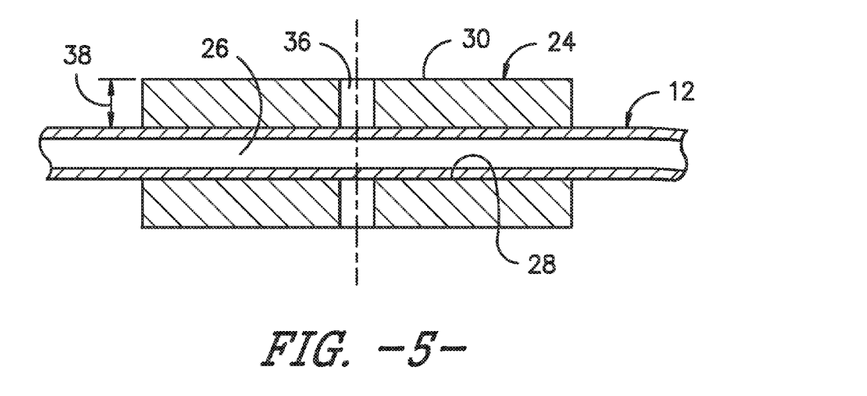
FIG. 5 illustrates a side, cross-sectional view of the embodiment of FIG. 4 with a catheter inserted therethrough in accordance with aspects of the invention.

In additional embodiments, as shown in FIGS. 4, 6, 7, and 8, the discontinuities 32 may extend from the bore 26 of the insert 24 through a portion of the thickness 38 of the insert 24. In alternative embodiments, as shown in FIG. 5, the discontinuities 32 may extend the entire thickness 38 of the insert 24 and may also extend through the exterior wall 30, as shown by through-hole 36.

In still further embodiments, the discontinuities 32 may be spaced equally about the interior wall 28 of the insert 24. For example, as shown in FIGS. 8(B) and 8(C), the discontinuities 32 are spaced approximately 90 degrees apart. In further embodiments, the discontinuities may be spaced more than 90 degrees apart or less than 90 degrees apart. In alternative embodiments, the plurality of discontinuities 32 may be spaced randomly about the interior wall 28.

Referring particularly to FIG. 4(B), in various embodiments, when the catheter 12 is inserted through the bore 26, a plurality of cavities 34 are formed by the catheter 12 and the plurality of discontinuities 32. More specifically, the insert 24 is configured to squeeze or apply a pressure to the catheter 12 when the catheter 12 is inserted therethrough so as to form the one or more cavities 34. Thus, the one or more cavities 34 are configured to receive and/or collect a liquid medium therein. For example, oftentimes, when the catheter 12 is inserted into a patient using ultrasonic gel, the proximal end of the catheter 12 may become contaminated with gel, making it difficult to maintain a connection between the catheter 12 and the catheter connector 10. Thus, the one or more cavities 34 described herein are configured to provide an escape for the gel (or any other liquid medium) such that the connection between the catheter 12 and the catheter connector 10 remains secure. It should be understood that the cavities 34 also provide an escape location for any other liquid medium, e.g. medicine, blood, saliva, or similar, if such a liquid medium becomes trapped in the catheter connector 10.

Figure 7:
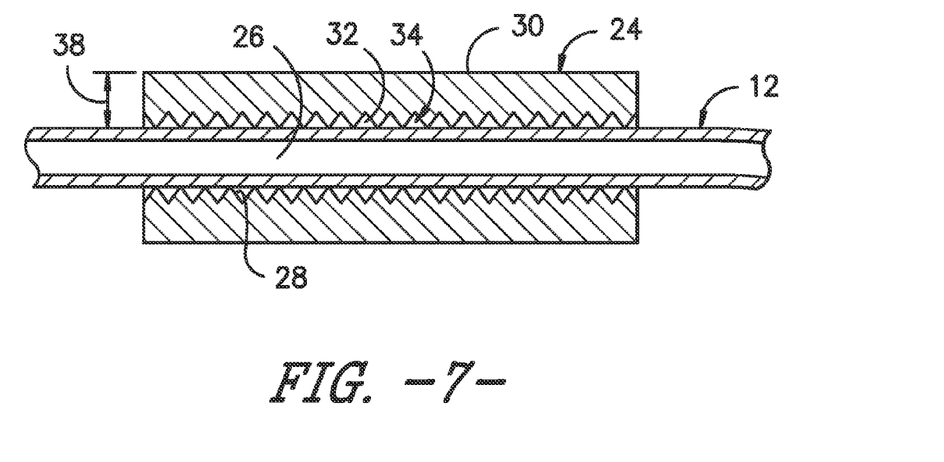
FIG. 7 illustrates a side, cross-sectional view of the embodiment of FIG. 6 a catheter inserted therethrough in accordance with aspects of the invention.
Figure 8:
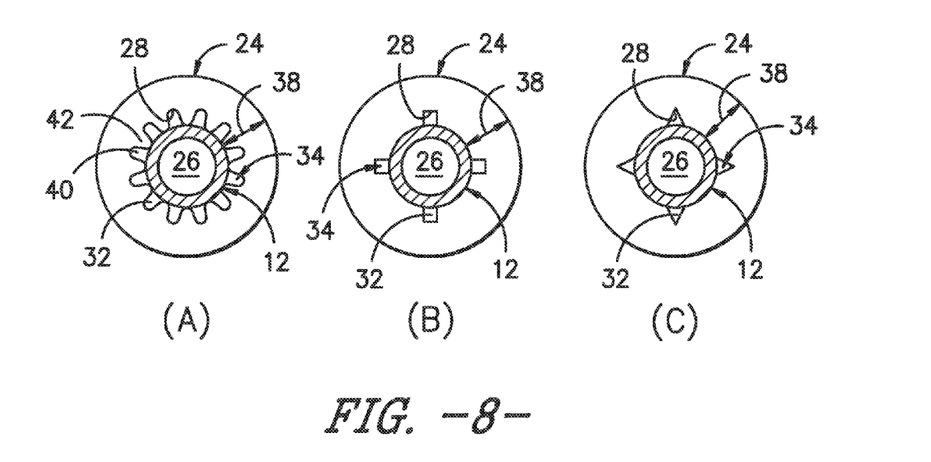
FIG. 8 illustrates front, cross-sectional views of various embodiments of a catheter connector insert in accordance with aspects of the invention.

Referring still to FIGS. 4, 7, and 8, the cavities 34 may include any suitable cross-sectional shape. For example, as shown in FIGS. 4(B), 7, and 8(C), each of the cavities 34 has a triangular cross-section. Alternatively, as shown in FIG. 8(B), each of the cavities 34 has a square cross-section. In still further embodiments, the cavities 34 may have any suitable cross-section of any shape and/or size so as to accommodate a liquid medium as described herein.

It should also be understood that the insert 24 may be constructed of any suitable material. For example, in certain embodiments, the insert 24 may be constructed of a flexible material, such as a rubber material, a polymeric material, a silicone material, an elastomeric material, or similar. More specifically, in various embodiments, the insert 24 may be constructed of silicone, kraton, polyisoprene, polyurethane, styrene butadiene, latex, and/or any other suitable flexible material. In alternative embodiments, the insert 24 may also be constructed of a rigid material, such as metal.

Figure 9:
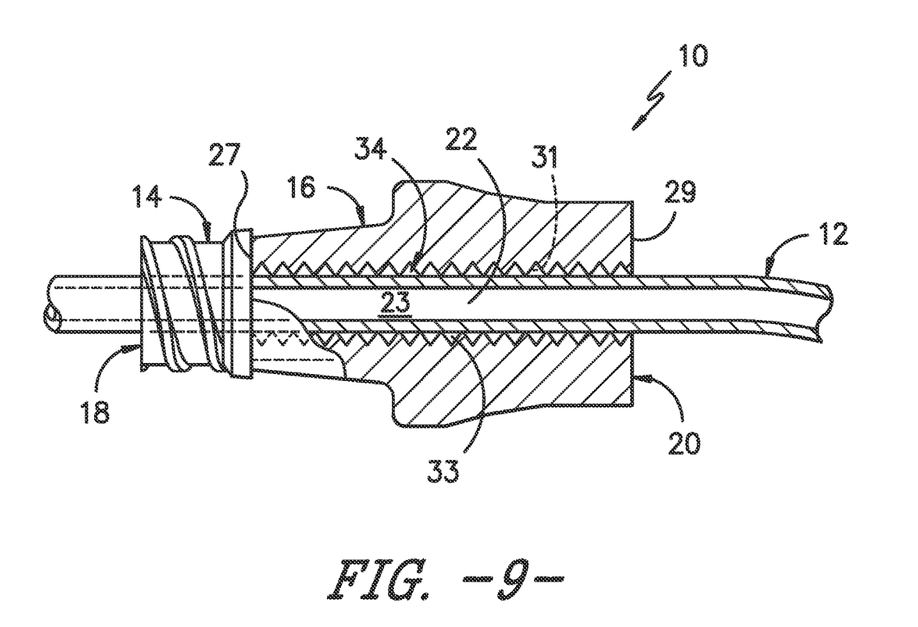
FIG. 9 illustrates a cross-sectional view of another embodiment of a catheter connector in accordance with aspects of the invention.

Referring now to FIG. 9, another embodiment of a catheter connector 10 configured therein according to the present disclosure is illustrated. As shown, the catheter connector 10 is similar to the embodiment of FIGS. 1 and 2. For example, the connector 10 has a body 16 with a proximal end 18 and a distal end 20. The body defines a hollow interior 22 extending from the proximal end 18 to the distal end 20. Further, a proximal end port 14 is configured with the proximal end of the body 16 for mating communication with a fluid delivery device. The connector 10 is manufactured such that the hollow interior 22 defines a bore 23 therethrough that is configured to receive the catheter 12 at least partially therethrough. Further, the bore 23 includes an interior wall 31 having the at least one discontinuity 33. Thus, in such an embodiment, the hollow interior 22 of the connector 10 itself includes the at least one discontinuity 33 and therefore, does not require the use of an additional insert. Similar to the other embodiments described herein, when the catheter 12 is inserted through the bore 23, at least one cavity 34 is formed by the catheter 12 and the at least one discontinuity 33. Thus, the cavity 34 is configured to collect a liquid medium therein. It should be understood that the one or more discontinuities 33 of the connector 10 may be include any of the features as described herein, e.g. having any suitable shape and/or size, etc.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:
1. A catheter connector, comprising:
   a body having a proximal end and a distal end, said body defining a hollow interior extending from said proximal end to said distal end;
   a proximal end port configured with said proximal end of body for mating communication with a fluid delivery device; and
   an insert configured within the hollow interior, said insert defining a bore therethrough, said bore configured to receive a catheter at least partially therethrough, said bore comprising an interior wall and an exterior wall defining a thickness therebetween, said interior wall comprising a plurality of discontinues, wherein, when the catheter is inserted through said bore, a plurality of individual closed cavities are formed by the catheter and each of the plurality of discontinuities of the insert, each of said individual closed cavities configured to collect and trap a liquid medium therein.

2. The catheter connector of claim 1, wherein said exterior wall of said insert is configured within said hollow interior of said body so as to provide a friction fit between said insert and said body.

3. The catheter connector of claim 1, wherein said plurality of discontinuities extend from said bore through a portion of the thickness of said insert.

4. The catheter connector of claim 1, wherein said plurality of discontinuities are spaced circumferentially about said interior wall.

5. The catheter connector of claim 4, wherein said plurality of discontinuities are spaced equally about said interior wall.

6. The catheter connector of claim 4, wherein said plurality of discontinuities are spaced randomly about said interior wall.

7. The catheter connector of claim 1, wherein said plurality of discontinuities comprise at least one of a rib, a ridge, a protrusion, a peak, a valley, a channel, a through hole, an aperture, or a void.

8. The catheter connector of claim 1, wherein said plurality of discontinuities comprises a plurality of peaks spaced circumferentially about said interior wall, said plurality of peaks spaced apart by a plurality of valleys.

9. The catheter connector of claim 8, wherein each of said plurality of peaks and each of said plurality of valleys comprise at least one non-arcuate edge.

10. The catheter connector of claim 8, wherein each of said plurality of closed cavities comprise a triangular cross-section.

11. The catheter connector of claim 8, wherein each of said plurality of peaks and each of said plurality of valleys comprise at least one arcuate edge.

12. The catheter connector of claim 1, wherein said insert comprises a flexible material, wherein said flexible material comprises at least one of or a combination of the following: a rubber material, a polymeric material, a silicone material, or an elastomeric material.

13. A catheter connector, comprising:
a body having a proximal end and a distal end, said body defining a hollow interior extending from said proximal end to said distal end;

a proximal end port configured with said proximal end of body for mating communication with a fluid delivery device, wherein said hollow interior defines a bore therethrough, said bore configured to receive a catheter at least partially therethrough, said bore comprising an interior wall comprising a plurality of discontinuities, wherein, when the catheter is inserted through said bore, a plurality of individual closed cavities are formed by the catheter and each of the plurality of discontinuities of the insert, each of said individual closed cavities configured to collect and trap a liquid medium therein.

14. An insert for a catheter connector, comprising:
a body configured to fit within a hollow interior of the catheter connector, said body having a proximal end and a distal end, said body comprising a bore extending from said proximal end to said distal end, said bore configured to receive a catheter at least partially therethrough, said bore comprising an interior wall comprising a plurality of discontinuities, wherein, when the catheter is inserted through said bore, a plurality of individual closed cavities are formed by the catheter and each of the plurality of discontinuities, each of said individual closed cavities configured to collect and trap a liquid medium that may enter the catheter connector, thereby maintaining a secure connection between the catheter and the catheter connector.

15. The insert of claim 14, wherein said plurality of discontinuities are spaced circumferentially about said interior wall.

16. The insert of claim 15, wherein said insert comprises a flexible material, said flexible material comprising at least one of or a combination of the following: a rubber material, a polymeric material, a silicone material, or an elastomerie material.

17. The insert of claim 14, wherein said plurality of discontinuities comprise at least one of a rib, a ridge, a protrusion, a peak, a valley, a channel, a through hole, an aperture, or a void.

18. The insert of claim 14, wherein said plurality of discontinuities comprises a plurality of peaks spaced circumferentially about said interior wall and spaced apart by a plurality of valleys.

19. The insert of claim 18, wherein each of said plurality of closed cavities comprise a triangular cross section.

* * * * *

UNITED STATES PATENT AND TRADEMARK OFFICE
CERTIFICATE OF CORRECTION

PATENT NO. : 9,925,364 B2
APPLICATION NO. : 14/282087
DATED : March 27, 2018
INVENTOR(S) : Steve Saeed Khalaj and Kenneth Chen-Tse Hsu Page 1 of 1

It is certified that error appears in the above-identified patent and that said Letters Patent is hereby corrected as shown below:

In the Claims

Claim 1 (Column 7, Line 2):
"discontinues" should read -- "discontinuities" --

Signed and Sealed this
First Day of February, 2022

Drew Hirshfeld
*Performing the Functions and Duties of the
Under Secretary of Commerce for Intellectual Property and
Director of the United States Patent and Trademark Office*